United States Patent [19]

Bogden

[11] Patent Number: 5,411,943
[45] Date of Patent: May 2, 1995

[54] HEPATOMA TREATMENT WITH SOMATOSTATIN ANALOGS

[75] Inventor: Arthur E. Bogden, Hopedale, Mass.
[73] Assignee: Biomeasure, Inc., Milford, Mass.
[21] Appl. No.: 840,881
[22] Filed: Feb. 25, 1992
[51] Int. Cl.⁶ ................................. A61K 7/06
[52] U.S. Cl. ............................... 514/16; 514/9; 514/11; 514/14; 514/15; 514/17
[58] Field of Search ............... 514/9, 11, 14–17; 530/311, 327–329

[56] References Cited

U.S. PATENT DOCUMENTS 5,073,541 12/1991 Taylor et al. .................... 514/16

OTHER PUBLICATIONS

Chou et al., The American Society for Clinical Investigation, Inc. 79:175, 1987.

Primary Examiner—Lester L. Lee
Attorney, Agent, or Firm—Fish & Richardson

[57] ABSTRACT

A method for treating liver cancer in a mammalian subject. The method includes administering to the subject a composition which contains a therapeutically effective amount of an octapeptide of the following formula:

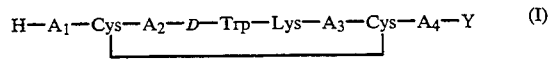

wherein, $A_1$ is D-$\beta$-Nal or D-Phe; $A_2$ is Phe, pentafluro-Phe, or p-substituted X-Phe where X is a halogen, $NH_2$, $NO_2$, OH, or $C_{1-3}$ alkyl; $A_3$ is Thr, Ser, Phe, Val, $\alpha$-aminobutyric acid, or Ile; $A_4$ is Thr, $\beta$-Nal, or Trp; and Y is $NH_2$ or OH; or a pharmaceutically acceptable salt or complex thereof.

28 Claims, 1 Drawing Sheet

HEPATOMA TREATMENT WITH SOMATOSTATIN ANALOGS

BACKGROUND OF THE INVENTION

This invention relates to a therapeutic process for treating liver cancer in a mammalian subject with octapeptide analogs of somatostatin.

A number of somatostatin analogs which exhibit growth hormone release inhibiting activity have been described in the literature, including analogs containing fewer than the naturally occurring fourteen amino acid residues.

For example, Coy et al., U.S. Pat. No. 4,485,101, hereby incorporated by reference, describes octapeptides which are effective to inhibit growth hormone release as well as to inhibit insulin, glucagon, and pancreatic exocrine secretion.

SUMMARY OF THE INVENTION

In general, the present invention features a method for treating hepatoma, or liver cancer, in a mammalian subject by administering to the subject a composition containing a therapeutically effective amount of a somatostatin analog. The somatostatin analog which can be used for the above-described treatment is an octapeptide of the following formula:

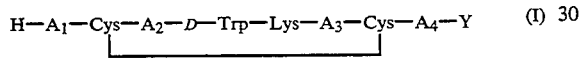

wherein, $A_1$ is D-$\beta$-Nal or D-Phe; $A_2$ is Phe, pentafluro-Phe, or p-substituted X-Phe where X is a halogen, $NH_2$, $NO_2$, OH, or $C_{1-3}$ alkyl; $A_3$ is Thr, Ser, Phe, Val, $\alpha$-aminobutyric acid, or Ile; $A_4$ is Thr, $\beta$-Nal, or Trp; and Y is $NH_2$ or OH; or a pharmaceutically acceptable salt or complex thereof.

In formula (I), the N-terminus is at the left and the C-terminus at the right in accordance with the conventional representation of a polypeptide chain. $A_1$, $A_2$, $A_3$, $A_4$, Cys, Trp, or the like stands for an amino acid residue, —NH—CH(R)—CO—, where R is the identifying group of an amino acid, e.g., R is —$CH_2OH$ for Ser. Also, where the amino acid residue is optically active, it is the L-form configuration that is intended unless D-form is expressly designated. Nal is the abbreviation for naphthylalanine. Pentafluoro-Phe is a Phe with its benzene ring fully substituted by fluorines. An example of a p-substituted X-Phe is Tyr, i.e., X is OH.

Note that the bond line between the two Cys residues in formula (I) indicates intramolecular cyclization by formation of a disulfide bridge. The bond line, however, will be omitted for convenience in the specification and claims set forth below.

Preferred embodiments of the invention are the above-described therapeutic use of octapeptides of formula (I) wherein $A_1$ is D-$\beta$-Nal or D-Phe; $A_2$ is Phe or Tyr; $A_3$ is Thr or Val; $A_4$ is Thr, $\beta$-Nal, or Trp; and Y is $NH_2$ or OH; or a pharmaceutically acceptable salt or complex thereof.

Particularly preferred octapeptides to be used are:

H-D-$\beta$-Nal-Cys-Tyr-D-Trp-Lys-Val-Cys-Thr-$NH_2$;

H-D-Phe-Cys-Tyr-D-Trp-Lys-Val-Cys-$\beta$-Nal-$NH_2$;

H-D-$\beta$-Nal-Cys-Tyr-D-Trp-Lys-Thr-Cys-Thr-$NH_2$;

H-D-Phe-Cys-Tyr-D-Trp-Lys-Thr-Cys-$\beta$-Nal-$NH_2$;

H-D-Phe-Cys-Phe-D-Trp-Lys-Thr-Cys-Thr-OH;

H-D-Phe-Cys-Phe-D-Trp-Lys-Val-Cys-Thr-$NH_2$;

and

H-D-Phe-Cys-Tyr-D-Trp-Lys-Val-Cys-Trp-$NH_2$.

It is also preferred that the therapeutic composition further includes a pharmaceutically acceptable carrier substance, e.g., mannitol, lactose, magnesium carbonate, or phospholipid with which the octapeptide can form a micelle.

It is generally the case that peptides such as somatostatin analogs are stable at acidic pH, but rapidly degrade under basic conditions and/or in the presence of pancreatic enzymes (trypsin/chymotrypsin). Thus, when given orally, such substances need to be protected against pancreatic enzymes and the intestinal environment (pH and bacteria). Furthermore, a co-transport agent such as glucose might be necessary for oral bioavailability.

Examples of therapeutic compositions that are suitable for oral administration include a pill, tablet, capsule, or liquid. When the composition is administered orally to the subject, it is particularly preferred that the octapeptide be coated with a substance capable of protecting it from degradation in the subject's stomach for a sufficiently long period of time. This allows all or most of the octapeptide molecules to pass into and adsorbed by the small intestine in their intact form.

Alternatively, the composition can be prepared in a suitable form, such as a liquid, for administration into the subject via a parenteral route, such as intravenous or subcutaneous administration. Other routes of administration include transdermal (e.g., topical—using cream with or without a penetration enhancer, or iontophoretic) and transmucosal (e.g., nasal, vaginal, buccal, bronchial, tracheal, or pulmonary). Moreover, targeted delivery to the tumor site by perfusion of the liver can be performed.

The therapeutic composition can also be in the form of a biodegradable sustained release formulation suitable for intramuscular or subcutaneous administration. For maximum efficacy, zero order release is most preferred. Zero order release can be obtained by means of an implantable or external pump, such as a Zyklomat BT1 Peristaltic pump (Ferring Laboratories, Suffern, N.Y.), to administer the therapeutic composition.

The terms "therapeutically effective amount", "pharmaceutically acceptable salt or complex" and "pharmaceutically acceptable carrier" will be defined or exemplified respectively below.

Other features and advantages of the invention will be apparent from the following description of the preferred embodiments thereof, and from the claims.

DETAILED DESCRIPTION OF PREFERRED EMBODIMENTS

The drawings will first be briefly described.

DRAWING

Figure 1:
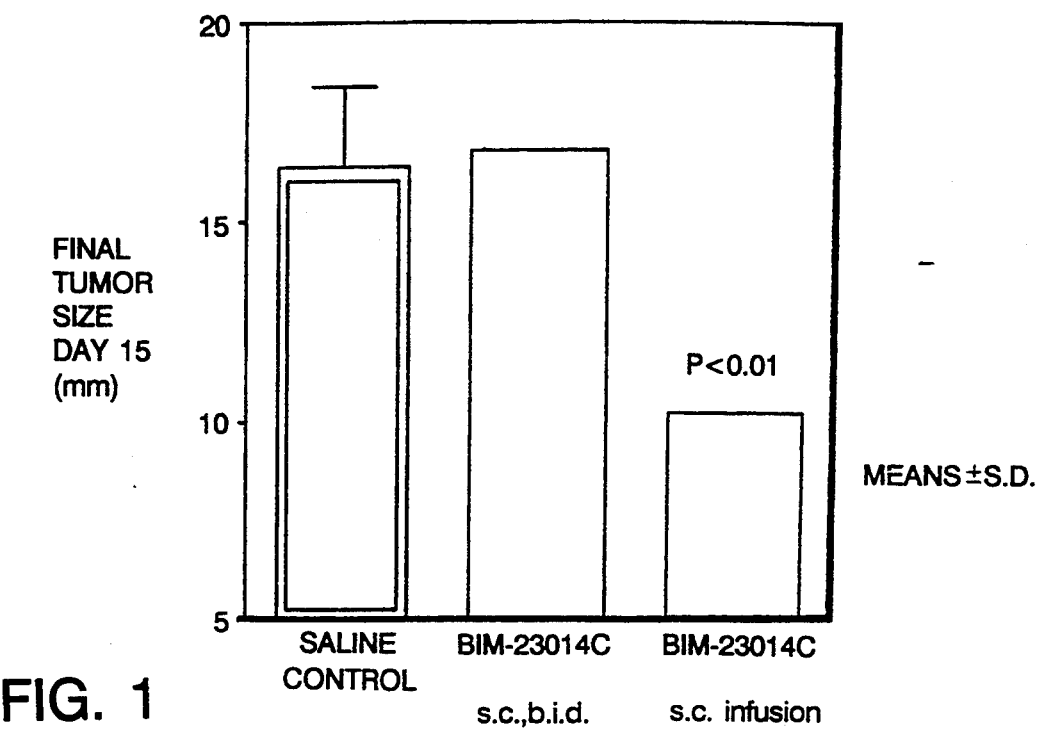
Figure 2:
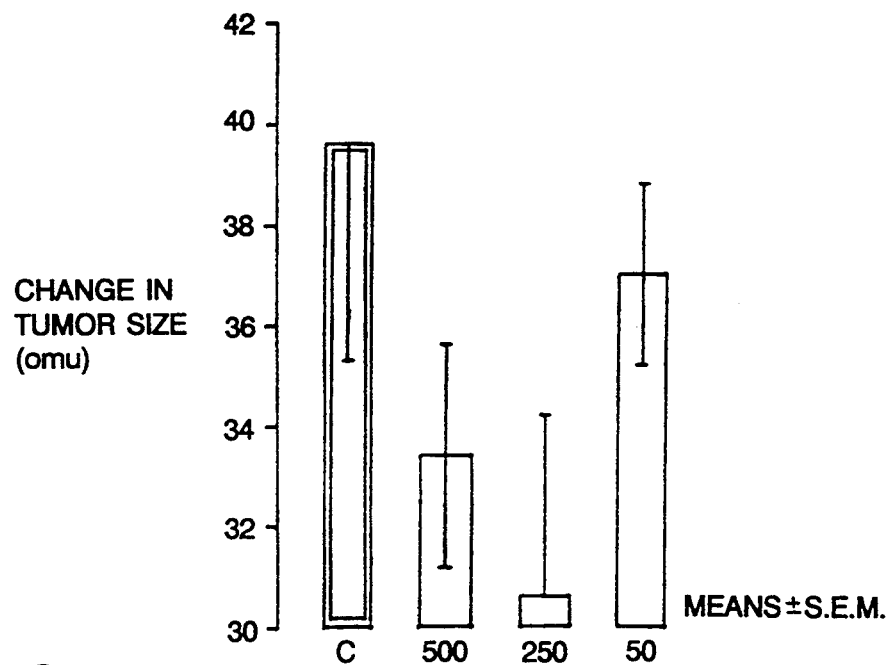

FIGS. 1 and 2 are graphs showing the growth inhibitory effect of a somatostatin analog on hepatoma cells implanted in athymic female mice.

STRUCTURE

The compounds used in the invention have the general structure, i.e., formula (I), recited above in "Summary of the Invention". They are all octapeptide analogs of somatostatin which have a Cys residue at position 2, a D-Trp residue at position 4, a Lys residue at position 5 and a second Cys residue at position 7; and optional modifications at positions 1 (i.e., $A_1$), 3 (i.e., $A_2$), 6 (i.e., $A_3$) and 8 (i.e., $A_4$). It has been found that D-$\beta$-Nal at position 1, Tyr at position 3, Val at position 6 and Thr at position 8 are modifications which particularly enhance the activity of inhibiting growth of hepatoma cells.

The compounds can be provided in the form of pharmaceutically acceptable salts, e.g., acid addition salts, or metal complexes, e.g., with zinc, iron or the like. Illustrative examples of acid addition salts are those with organic acids such as acetic, lactic, pamoic, maleic, citric, malic, ascorbic, succinic, benzoic, palmitic, suberic, salicylic, tartric, methanesulfonic or toluenesulfonic acid, those with polymeric acids such as tannic acid or carboxymethyl cellulose, and those with inorganic acids such as hydrochloric acid, hydrobromic acid, sulfuric acid or phosphoric acid.

SYNTHESIS

The synthesis of an octapeptide with an amide C-terminus disclosed above follows. Other such octapeptides used in the invention can be prepared by making appropriate modifications, within the ability of someone of ordinary skill in this field, of the synthetic method disclosed herein.

The first step in the synthesis of H-D-$\beta$-Nal-Cys-Tyr-D-Trp-Lys-Val-Cys-Thr-NH$_2$ was preparation of the intermediate, tert-butyloxycarbonyl("Boc")-D-$\beta$-Nal-S-p-methylbenzyl-Cys-Tyr-D-Trp-$\epsilon$-N-benzyloxycarbonyl-Lys-Val-S-p-methylbenzyl-Cys-O-benzyl-Thr-benzhydrylamine resin, as follows.

Benzhydrylamine-polystyrene resin (Vega Biochemicals, Inc.) in the chloride ion form was placed in the reaction vessel of a Beckman 990B peptide synthesizer programmed to perform the following reaction cycle: (a) methylene chloride; (b) 33% trifluoroacetic acid in methylene chloride (two times, for 1 min. and 25 min. each); (c) methylene chloride; (d) ethanol; (e) methylene chloride; (f) 10% triethylamine in chloroform.

The neutralized resin was first stirred with Boc-O-benzyl-threonine and diisopropylcarbodiimide (1.5 mmole each) in methylene chloride for 1 hr. and the resulting amino acid resin was then cycled through steps (a) to (f) in the above wash program. The following amino acids (1.5 mmole) were then coupled successively by the same procedure: Boc-S-methylbenzyl-Cys, Boc-Val, Boc-$\epsilon$-N-benzyloxycarbonyl-Lys, Boc-D-Trp, Boc-Tyr, Boc-S-p-methylbenzyl-Cys, and Boc-D-$\beta$-Nal.

Thereafter, the resin was washed and dried and then mixed with anisole (4 ml) and anhydrous hydrogen fluoride (36 ml) at 0° C. and stirred for 45 min. Alternatively, one can also use thioanisole, trifluoroacetic acid, and trifluoromethane sulfonic acid at a ratio of 1:90:9, for 6 hr. Excess hydrogen fluoride was evaporated rapidly under a stream of dry nitrogen and the free peptide was precipitated and washed with ether. The crude peptide thus obtained was then dissolved in 800 ml of 90% acetic acid to which was added I$_2$ in methanol until a permanent brown color appeared. The solution was then stirred for 1 hr. before removing the solvent in vacuo. The resulting oil was dissolved in a minimum volume of 50% acetic acid and eluted on a Sephadex G-25 column (2.5 × 100 mm). Fractions containing a major component as shown by UV absorption and thin layer chromatography ("TLC") were then pooled, evaporated to a small volume, and applied to a column (2.5 × 50 cm) of Whatman LRP-1 octadecylsilane (15-20 $\mu$M).

The column was eluted with a linear gradient of 10-50% acetonitrile in 0.1% trifluoroacetic acid in water. Fractions were examined by TLC and analytical high performance liquid chromatography ("HPLC") and pooled to give maximum purity and if desired, a different salt was prepared, e.g., acetate or phosphate. Repeated lyophilization of the solution from water gave 170 mg of the product as a white, fluffy powder.

The synthetic product was found to be homogeneous by both HPLC and TLC. Amino acid analysis of an acid hydrolysate confirmed the composition of the octapeptide.

Also synthesized according to a method similar to that described above was, among others, H-D-$\beta$-Nal-Cys-Tyr-D-Trp-Lys-$\alpha$-aminobutyric acid-Cys-Thr-NH$_2$, another octapeptide analog of somatostatin with an amide C-terminus which can be employed for the treatment of liver cancer.

The methods for synthesizing octapeptide analogs of somatostatin with a carboxyl C-terminus are well documented and are within the ability of a person of ordinary skill in the art. For example, synthesis of the peptide H-D-Phe-Cys-Phe-D-Trp-Lys-Thr-Cys-Thr-OH described above can be achieved by following the protocol set forth in Example 1A of U.S. Pat. No. 4,395,403, which is hereby incorporated by reference.

ASSAYS FOR DETERMINING ANTI-HEPATOMA ACTIVITY

Tumor System

The M5123 hepatoma cells, obtained from Dr. H. P. Morris at the National Cancer Institute, were induced in the Buffalo strain of rats by ingestion of N-(2-fluorenylphthalamic acid) and established in serial transplantation. Implantation of the M5123 hepatoma cells in an immunodeficient athymic mouse or Buffalo strain rat reproducibly results in a progressively growing, lethal tumor.

Assay System

To determine the growth inhibitory effect of bombesin analogs on hepatoma cells, two in vivo assay systems, the subcutaneous tumor assay in the syngeneic Buffalo strain rat and the subrenal capsule assay using the immunodeficient athymic nude mouse were employed.

(1) Subcutaneous Assay

In the subcutaneous assay, tumor grafts are implanted subcutaneously and treatment can be initiated at any selected time after the implantation.

In this assay, 20 male Buffalo strain rats were implanted s.c., right flank, with a 2 mm$^3$ mince of the M5123 hepatoma in the a.m. of day zero. The animals were individually identified and then randomized 10 rats in the control and 5 rats per test group. Treatment was initiated in the p.m. and continued as shown in the Table 1. An somatostatin analog used in the invention, H-D-$\beta$-Nal-Cys-Tyr-D-Trp-Lys-Val-Cys-Thr-NH$_2$ (code name: BIM-23014), was administered b.i.d. Monday through Friday, and as a single total daily dose on Saturday and Sunday. Tumor sizes were determined with Vernier calipers twice weekly and size calculated as the average of two diameters (length+width/2) mm.

(2) Subrenal Capsule Assay ("SRCA")

SRCA was designed as a rapid in vivo method for testing chemotherapeutic agents against tumor xenografts prepared from solid malignancies. As an antitumor screening procedure, tumors, both human and murine, can be tested as xenografts in athymic female mice. For detailed description of this assay, see Bogden, A. E. et al. A rapid screening method for testing chemotherapeutic agents against human tumor xenografts. In: Proc. Symp. Use of Athymic (Nude) Mice in Cancer Research, p. 231, Edited by Houchens et al., Gustav Fisher, N.Y. (1978).

Fundamental to its design are the considerations that solid tumors are composed of heterogeneous cell populations (heterogeneous in terms of biosynthetic functions, growth potential, drug and growth factor sensitivity, and expression of antigens or receptors), and that the complexity of epithelial/stromal relationship not only affects tumor growth, but also affects other functional characteristics as well.

By utilizing tumor fragments for subrenal capsule implantation, the integrity of both cell membrane which are essential for receptor reactions, cell-to-cell contact and the spatial relationship of the cell populations, and tissues within the tumor fragments which are essential for the stability of autocrine and paracrine effects are maintained. Tumor response to drug or biological response modifier, such as a somatostatin analog, in such a relatively intact microenvironment is measured as a net response of multiple cell populations, both clonogenic and non-clonogenic. It also more realistically provides the accessibility barriers of the existing intercellular environment.

Further, an in situ determination of tumor xenograft size at time of implantation and again at termination of the assay, permits use of the very simple parameter of change in tumor size for evaluating tumor sensitivity to the analog. Since the initial measurement provides each xenograft with its own baseline for evaluating drug effects, one can measure tumor response to drugs in terms of progression, stabilization, partial remission and complete remission, which are parameters that have clinical relevance.

In this assay, xenografts prepared from the transplantation-established M5123 hepatoma were first implanted in immunodeficient athymic female mice, followed by treatment with BIM-23014, in assays of 10-day duration. Thirty two athymic female mice were implanted under the renal capsule with 1 mm cubed grafts of the M5123 rat hepatoma on day zero. Treatment with the analog was initiated on day one at 500, 250 and 50 µg per injection, s.c., b.i.d., on a q.d. 1-9 schedule. On day 10, the mice were sacrificed, the kidney was removed and the size of the tumor was measured to determine changes in tumor size between day 0 and day 10.

More specifically, the size of the tumor was measured in situ by means of a stereoscope, which was fitted with an ocular micrometer calibrated in ocular units (OMU, 10 OMU=1 mm). For each tumor, two perpendicular diameters were measured and the difference in mean tumor diameter over the 10-day period was calculated.

Results

The results of the subcutaneous assay are summarized in Table 1 and FIG. 1 (illustrated as a bar graph). The M5123 hepatoma is a very rapidly growing malignancy so that the assay was terminated on day 15 before extensive tumor ulcerations developed.

TABLE 1

| Treatment | Final Tumor Size* Day 15 (mm) | Percent Test/Control |
|---|---|---|
| 1. Saline vehicle control, 0.2 ml, inj., s.c., b.i.d., q.d. 0-15 | 16.4 ± 2.0 | — |
| 2. 500 µg analog/inj., s.c., b.i.d., q.d. 0-15 | 16.8 ± 2.4 | 102 |
| 3. 500 µg analog/inj., s.c., infusion b.i.d., q.d. 0-15 | 10.2 ± 5.6** | 62 |

*Data expressed as means ± S.D.
**Significance of difference form control Student's tTest: $p < 0.01$.

Subcutaneous administration of BIM-23014 on the flank opposite from the tumor induced no tumor inhibitory effects at the dose level used. However, when administered at the same dose level as a s.c. perilesional infusion, growth of the M5123 hepatoma was significantly inhibited ($p < 0.01$).

Since neoplasms maintain autonomous growth by autocrine and paracrine growth factors, the importance of attaining therapeutic concentrations of an antigrowth factor such as BIM-23014 at the tumor site is emphasized in this study. There was no evidence of systemic toxic effects from treatment as would be indicated by body weight loss. Control Final Body Weight/Initial Body Weight ratio was 1.15, as compared to 1.06 for group 2 and 1.12 for group 3.

Shown in FIG. 2 and Table 2 is the effect of BIM-23014, in various dosages, on the growth of hepatoma cells implanted in athymic mice. At a dosage of 250 µg/injection, s.c., b.i.d., q.d. 1-9, this somatostatin analog effected a significant reduction, i.e., about 25%, in the growth of the tumor. This analog, when administered at a lower dose (50 µg) and at a higher dose (500 µg) exhibited slightly less antitumor activity (7% and 16% inhibition, respectively), producing an inverted bell-shaped dose response.

TABLE 2

| Treatment | Change in Tumor Size (omu) | % Test/Control** |
|---|---|---|
| Saline vehicle control, 0.2 ml, i.p., q.d. 1-9 | 39.63 ± 4.85 | — |
| 500 µg analog/inj., s.c., b.i.d., q.d. 1-9 | 33.38 ± 2.19 | 84 |
| 250 µg analog/inj., s.c., b.i.d., q.d. 1-9 | 30.56 ± 3.61 | 77 |
| 50 µg analog/inj., s.c., b.i.d., q.d. 1-9 | 37.00 ± 1.80 | 93 |

*Change in tumor size between day 0 and day 10 in ocular micrometer units (OMU) presented as means ± s.e.m.
**% Test/Control = Test tumor size/Control tumor size × 100

Use

Octapeptide analogs of somatostatin, as shown in formula (I) can be used for the in vivo treatment of liver cancer.

The amount to be administered, will depend upon the condition being treated, the route of administration chosen, and the specific activity of the analog, and ultimately will be decided by the attending physician or veterinarian. Such amount of the active analog as determined by the attending physician or veterinarian is referred to herein as a "therapeutically effective amount" and is in the range of 10 μg/kg/day to 500 μg/kg/day.

The octapeptide analog may be administered by any route appropriate to the condition being treated. Preferably, the analog is injected into the bloodstream of the subject being treated. However, it will be readily appreciated by those skilled in the art that the route, such as intravenous, subcutaneous, intramuscular, intraperitoneal, nasal, oral, etc., will vary with the condition being treated and the activity of the analog being used.

While it is possible for the somatostatin analog to be administered as the pure or substantially pure compound, it is preferable to present it as a pharmaceutical formulation or preparation.

The formulations to be used in the present invention, for both humans and animals, comprise any of the octapeptide analogs as described above, together with one or more pharmaceutically acceptable carriers therefor, and optionally other therapeutic ingredients.

The carrier must be "acceptable" in the sense of being compatible with the active ingredient(s) of the formulation (and preferably, capable of stabilizing peptides) and not deleterious to the subject to be treated. Desirably, the formulation should not include oxidizing agents or other substances with which peptides are known to be incompatible. For example, somatostatin analogs in the cyclized form are oxidized; thus, the presence of reducing agents as excipients could lead to an opening of the cystine disulfur bridge. On the other hand, highly oxidative conditions can lead to the formation of cysteine sulfoxide and to the oxidation of Tryptophane. Consequently, it is important to carefully select the excipient. As pointed out previously, pH is another key factor and it is necessary to buffer the product under slightly acidic conditions (pH 5 to 6).

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary as in the case of tablets, forming the product into the desired shape and size.

Formulations suitable for intravenous administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

OTHER EMBODIMENTS

The foregoing description has been limited to specific embodiments of this invention. It will be apparent, however, that variations and modifications may be made to the invention, with the attainment of some or all of the advantages of the invention. Such embodiments are also within the scope of the following claims.

What is claimed is:

1. A method for treating hepatoma in a mammalian subject, which method includes administering to said subject a composition comprising a therapeutically effective amount of an octapeptide of the following formula:

$$H\text{-}A_1\text{-}Cys\text{-}A_2\text{-}D\text{-}Trp\text{-}Lys\text{-}A_3\text{-}Cys\text{-}A_4\text{-}Y \qquad (I)$$

wherein, $A_1$ is D-$\beta$-Nal or D-Phe; $A_2$ is Phe, pentafluro-Phe, or p-substituted X-Phe where X is a halogen, $NH_2$, $NO_2$, OH, or $C_{1-3}$ alkyl; $A_3$ is Thr, Ser, Phe, Val, $\alpha$-aminobutyric acid, or Ile; $A_4$ is Thr, $\beta$-Nal, or Trp; and Y is $NH_2$ or OH; or a pharmaceutically acceptable salt or complex thereof.

2. The method of claim 1, wherein $A_1$ is D-$\beta$-Nal or D-Phe; $A_2$ is Phe or Tyr; $A_3$ is Thr, or Val; $A_4$ is Thr, $\beta$-Nal, or Trp; and Y is $NH_2$ or OH.

3. The method of claim 2, wherein said octapeptide is of the formula:

H-D-$\beta$-Nal-Cys-Tyr-D-Trp-Lys-Val-Cys-Thr-$NH_2$;

H-D-Phe-Cys-Tyr-D-Trp-Lys-Val-Cys-$\beta$-Nal-$NH_2$;

H-D-$\beta$-Nal-Cys-Tyr-D-Trp-Lys-Thr-Cys-Thr-$NH_2$;

H-D-Phe-Cys-Tyr-D-Trp-Lys-Thr-Cys-$\beta$-Nal-$NH_2$;

H-D-Phe-Cys-Phe-D-Trp-Lys-Thr-Cys-Thr-OH;

H-D-Phe-Cys-Phe-D-Trp-Lys-Val-Cys-Thr-$NH_2$;

or

H-D-Phe-Cys-Tyr-D-Trp-Lys-Val-Cys-Trp-$NH_2$.

4. The method of claim 2, wherein said octapeptide is of the formula:

H-D-$\beta$-Nal-Cys-Tyr-D-Trp-Lys-Val-Cys-Thr-$NH_2$.

5. The method of claim 1, wherein said composition is administered to said subject by perfusion of the liver.

6. The method of claim 1, wherein said composition is administered to said subject subcutaneously.

7. The method of claim 1, wherein said composition is administered to said subject intravenously.

8. The method of claim 1, wherein said composition is administered to said subject enterally.

9. The method of claim 1, wherein said composition is administered to said subject transdermally.

10. The method of claim 1, wherein said composition is administered to said subject transmucosally.

11. The method of claim 2, wherein said composition is administered to said subject by perfusion of the liver.

12. The method of claim 2, wherein said composition is administered to said subject subcutaneously.

13. The method of claim 2, wherein said composition is administered to said subject intravenously.

14. The method of claim 2, wherein said composition is administered to said subject enterally.

15. The method of claim 2, wherein said composition is administered to said subject transdermally.

16. The method of claim 2, wherein said composition is administered to said subject transmucosally.

17. The method of claim 3, wherein said composition is administered to said subject by perfusion of the liver.

18. The method of claim 3, wherein said composition is administered to said subject subcutaneously.

19. The method of claim 3, wherein said composition is administered to said subject intravenously.

20. The method of claim 3, wherein said composition is administered to said subject enterally.

21. The method of claim 3, wherein said composition is administered to said subject transdermally.

22. The method of claim 3, wherein said composition is administered to said subject transmucosally.

23. The method of claim 4, wherein said composition is administered to said subject by perfusion of the liver.

24. The method of claim 4, wherein said composition is administered to said subject subcutaneously.

25. The method of claim 4, wherein said composition is administered to said subject intravenously.

26. The method of claim 4, wherein said composition is administered to said subject enterally.

27. The method of claim 4, wherein said composition is administered to said subject transdermally.

28. The method of claim 4, wherein said composition is administered to said subject transmucosally.

* * * * *